United States Patent
Heiman et al.

(10) Patent No.: US 9,161,529 B2
(45) Date of Patent: Oct. 20, 2015

(54) STABLE AND NON-PRECIPITATING AQUEOUS COMPOSITIONS CONTAINING THE POTASSIUM SALT OF (S)-(+)-ABSCISIC ACID, AND METHODS OF THEIR PREPARATION AND USE

(71) Applicant: Valent BioSciences Corporation, Libertyville, IL (US)

(72) Inventors: Daniel F. Heiman, Libertyville, IL (US); Bala N. Devisetty, Buffalo Grove, IL (US); Peter D. Petracek, Grayslake, IL (US); Xiaozhong Liu, Vernon Hills, IL (US); John Lopez, Gurnee, IL (US); Derek D. Woolard, Zion, IL (US); Yueh Wang, Arlington Heights, IL (US); Gregory D. Venburg, Deerfield, IL (US); Prem Warrior, Chicago, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 14/275,056

(22) Filed: May 12, 2014

(65) Prior Publication Data

US 2014/0249030 A1 Sep. 4, 2014

Related U.S. Application Data

(63) Continuation of application No. 13/447,715, filed on Apr. 16, 2012, now Pat. No. 8,722,928, which is a continuation-in-part of application No. 12/011,846, filed on Jan. 30, 2008, now Pat. No. 8,318,976.

(60) Provisional application No. 60/898,550, filed on Jan. 31, 2007.

(51) Int. Cl.
| | |
|---|---|
| *C07C 63/06* | (2006.01) |
| *A01N 31/08* | (2006.01) |
| *A01N 25/22* | (2006.01) |
| *A01N 37/42* | (2006.01) |

(52) U.S. Cl.
CPC ............... *A01N 25/22* (2013.01); *A01N 37/42* (2013.01)

(58) Field of Classification Search
CPC ................................. C07C 63/06; A01N 31/08
USPC ................................................. 562/508, 509
See application file for complete search history.

(56) References Cited

U.S. PATENT DOCUMENTS

| | | |
|---|---|---|
| 4,209,530 A | 6/1980 | Visscher |
| 4,434,180 A | 2/1984 | Visscher |
| 5,201,931 A | 4/1993 | Abrams et al. |
| 5,518,995 A | 5/1996 | Abrams et al. |
| 6,004,905 A | 12/1999 | Abrams et al. |
| 6,074,986 A * | 6/2000 | Mulqueen et al. ............ 504/361 |
| 6,455,471 B1 | 9/2002 | Gubelmann-Bonneau et al. |
| 6,586,617 B1 * | 7/2003 | Tabuchi et al. ................ 558/394 |
| 2008/0207454 A1 | 8/2008 | Heiman et al. |

FOREIGN PATENT DOCUMENTS

GB 1251867 11/1971

OTHER PUBLICATIONS

International Search Report and Written Opinion issued Aug. 30, 2013.
Mauseth, "Botany an introduction to plant biology", 1991 Philadelphia Saundera pp. 348-415.
Raven et al., Biology of plants fifth edition, 1992 New York Worth. pp. 545-572.
Milborrow, "The chemistry and physiology of abscisic acid", Am. Rev. Plant Physiol. 1974, 25 pp. 259-307.
Zhang et. al., "Purification and identification of a 42-kilodalton abscisic acid-specific-binding protein from epidermis of broad bean leaves", Feb. 2002, Plant Physiology, vol. 128, pp. 714-725.
Finkelstein et al., "Abscisic Acid Biosynthesis and Response", 2002 The Arabidopsis Book, American Society of Plant Biologists, pp. 1-52.
Railton et al., "Effects of Abscisic Acid on the Levels of Endogenous Gibberellin-like Substames in Solanum Andigena", Plants (berl.) 112, 1973, pp. 65-69.
Blumenfeld et al., "Cuticular Penetration of Abscisic Acid", Planta (Berl.) 107, 1972, pp. 261-268.
Bonnafous et al., "Mouvelle Methode De Resolution Optique de L'Acide Abscisique", Tetrahedron Letters No. 13, 1973, pp. 1119-1122.
Yu et al., "Abscisic Acid Stimulates a Calcium-Dependent Protein Kinase in Grape Berry", Plant Physiology, vol. 140, Feb. 2006, pp. 558-579.
Kriedemann et al., "Abscisic Acid and Stomatal Regulation", Plant Physiology, 49, 1972, pp. 842-847.
Zeevart et al., "Metabolism and Physiology of Abscisic Acid", Ann. Rev. Plant Physiol Plant Mol. Biol., 39 1988, pp. 439-473.

* cited by examiner

*Primary Examiner* — Kamal Saeed
*Assistant Examiner* — Janet L Coppins
(74) *Attorney, Agent, or Firm* — Wood, Phillips, Katz, Clark & Mortimer

(57) ABSTRACT

The present invention generally relates to aqueous compositions containing salts of (S)-(+)-abscisic acid, the surfactant Atlox™ 4913, and the color stabilizers sodium citrate and sodium acetate, methods of their preparation, and methods of their agricultural use.

20 Claims, No Drawings

STABLE AND NON-PRECIPITATING AQUEOUS COMPOSITIONS CONTAINING THE POTASSIUM SALT OF (S)-(+)-ABSCISIC ACID, AND METHODS OF THEIR PREPARATION AND USE

RELATED APPLICATIONS

This application is a continuation of U.S. application Ser. No. 13/447,715, filed Apr. 16, 2012, which issued on May 13, 2014 as U.S. Pat. No. 8,722,928, which is a continuation-in-part of U.S. application Ser. No. 12/011,846, filed Jan. 30, 2008, which issued on November 27, 2012 as U.S. Pat. No. 8,318,976, which claims the benefit of U.S. Provisional Application Ser. No. 60/898,550 filed Jan. 31, 2007. The entire teachings of the above-referenced applications are incorporated herein by reference.

FIELD OF THE INVENTION

The present invention generally relates to color stable and non-precipitating aqueous compositions containing salts of (S)-(+)-abscisic acid, methods of their preparation, and methods of their agricultural use.

Abscisic acid ("(S)-(+)-abscisic acid" or "S-ABA") is a naturally occurring plant hormone which is found in all higher plants (Cutler and Krochko, 1999. Finkelstein and Rock, 2002). (S)-(+)-abscisic acid is involved in many major processes during plant growth and development including dormancy, germination, bud break, flowering, fruit set, general growth and development, stress tolerance, ripening, maturation, organ abscission, and senescence. (S)-(+)-abscisic acid also plays an important role in plant tolerance to environmental stresses, such as drought, cold, and excessive salinity.

The naturally occurring enantiomeric form of abscisic acid is (S)-(+)-abscisic acid. In some literature reports the other enantiomer, (R)-(−)-abscisic acid is seen to be biologically inactive. In other research, it has been reported that (R)-(−)-abscisic acid also has some biological activities, however, they are often different from those of the (S)-(+)-enantiomer. See, Zeevart, J. A. D. and Creelman, R. A. (1988) *Metabolism and Physiology of Abscisic Acid*, Annu Rev. Plant Physiol. Plant Mol. Biol. 39, 439-473. Thus, for use in a commercial agricultural product, the compositions of the present invention comprising (S)-(+)-abscisic acid as the active ingredient are preferable to the prior art compositions comprising racemic (R,S)-(±)-abscisic acid, because, in the best case for these prior art compositions, half of the racemic (R,S)-(±)-abscisic acid is inert, resulting in the need to purchase, formulate, package, ship, and apply twice as much material. In the worst case, the (R)-(−)-enantiomer in racemic (R,S)-(±)-abscisic acid can add undesirable side effects to the desired result given by the applied (S)-(+)-abscisic acid and potentially result in undesirable residual material in food crops and in the environment.

The stereochemistry of the side chain of naturally occurring abscisic acid produced biosynthetically by all green plants and some microorganisms is 2-cis-,4-trans. The (S)-(+)-2-trans-,4-trans-isomer of abscisic acid also occurs naturally, being produced photolytically by the action of sunlight on the (S)-(+)-2-cis-,4-trans-isomer. The (S)-(+)-2-trans-,4-trans-isomer is reported to be biologically inactive. See, P. E. Kreidelmann, et al., Plant Physiol. 49, 842-847 (1972), D. P. Zhang, et al., Plant Physiol. 128, 714-725, (2002) or X. C. Yu, et al., Plant Physiol. 140, 558-579 (2006).

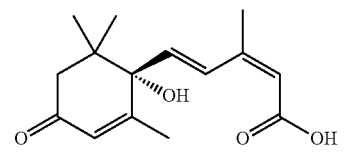

(S)-(+)-2-cis-,4-trans-abscisic acid

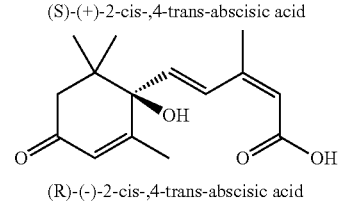

(R)-(−)-2-cis-,4-trans-abscisic acid

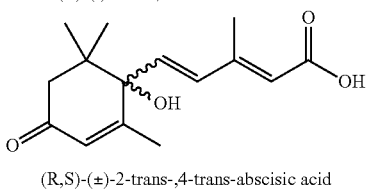

(R,S)-(±)-2-trans-,4-trans-abscisic acid

U.S. application Ser. No. 12/011,846 discloses salts of (S)-(+)-abscisic acid, and aqueous compositions containing salts of (S)-(+)-abscisic acid with an antimicrobial agent, a surfactant, and optionally one or more performance enhancing adjuvants, and optionally one or more stabilizers. The contents of U.S. application Ser. No. 12/011,846 are herein incorporated by reference.

A challenge with formulations of (S)-(+)-abscisic acid salts is the inability to maintain color stability. Previously, the color of aqueous soluble liquid formulations of (S)-(+)-abscisic acid changed during storage from a near colorless solution to a dark yellow or brown solution. Such a result is undesirable because the formulation can have an inconsistent cosmetic appearance which raises questions regarding formulation quality and efficacy and can lower the product's commercial appeal. Therefore, there is an unmet need in the art for (S)-(+)-abscisic acid salt formulations with greater color stability.

It is also common for prior art aqueous soluble liquid formulations of (S)-(+)-abscisic acid salts to form undesirable precipitates or particulate matter during storage or when mixed with other plant growth regulator products, such as ethephon, for application of both products as a tank mixture. This particulate matter renders the formulation unacceptable for use in a sprayer system or with an irrigation system because the particulate matter can potentially block components of the systems, such as emitters and nozzles. Additionally, precipitation of the active ingredient lowers the concentration of the active ingredient in the solution, thereby lowering the efficacy of the solution. Therefore, many prior art formulations are unacceptable because of precipitate formation.

SUMMARY OF THE INVENTION

The present invention is generally directed to color-stable and non-precipitating aqueous compositions containing salts of (S)-(+)-abscisic acid.

The present invention allows for improved concentrated formulations of (S)-(+)-abscisic acid that are more convenient to package, store, transport, handle, and apply to plants. These improved concentrated formulations are highly resistant to discoloration even under prolonged harsh environmental storage conditions. Further, these improved concentrated formulations can be easily mixed with water and other plant growth regulators, such as ethephon, without the formation of precipitates.

Compositions of the present invention generally comprise a salt of (S)-(+)-abscisic acid, the surfactant Atlox™ 4913, the color stabilizers sodium citrate and sodium acetate, at least one antimicrobial, and at least one solvent. Other components which enhance the long-term storage stability or the biological activity of the (S)-(+)-abscisic acid may optionally be included.

Applicants surprisingly discovered that inclusion of Atlox™ 4913 in compositions of the present invention improves microbial control and prevents precipitate formation in the formulations and its dilutions. Atlox™ 4913 is an acrylic copolymer solution and is available from Croda Crop Care.

Applicants also surprisingly discovered that the addition of sodium citrate and sodium acetate to compositions of the present invention produces a significant improvement in color stability. Sodium citrate and sodium acetate are both listed in the Food and Drug Administration's ("FDA") Select Committee on Generally Regarded as Safe Substances ("SCOGS") Database, and therefore, are desirable alternatives to color stabilizers utilized by the prior art that are undesirable or prohibited in pesticide formulations used on food crops in the United States.

Applicants have found that the formulations of this invention comprising potassium salts of (S)-(+)-abscisic acid show significant improvement over formulations of the prior art for treating plants. Specifically, previous formulations including salts of (S)-(+)-abscisic acid could not be mixed with ethephon because precipitates formed within a few hours, rendering the mixture without utility. Applicants found, however, that the improved formulation of the potassium salt of (S)-(+)-abscisic acid mixed well with ethephon and formed a stable solution. There is strong commercial demand for mixtures of (S)-(+)-abscisic with ethephon in some markets because the combination has proved useful for grape color development and has also proved useful to alter the sensory characteristics of the resulting wine. See, for example, U.S. application Ser. No. 12/266,633, Venburg, et al., *Synergistic Combination to Improve Grape Color and to Alter Sensory Characteristics of Wine*, the content of which is herein incorporated by reference. Ethephon is available from Bayer CropScience (GmbH, Frankfurt am Main, Germany).

DETAILED DESCRIPTION OF THE INVENTION

The present invention relates to liquid compositions of the potassium salt of (S)-(+)-abscisic acid. Abscisic acid is an optically active 15-carbon carboxylic acid. The structural formula of 2-cis-,4-trans-(S)-(+)-abscisic acid is set forth below:

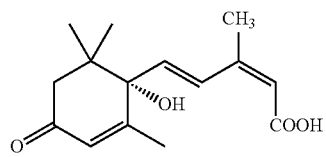 [SMILES: CC1=CC(=O)CC(C)(C)[C@@]1(O)/C=C/C(C)=C\C(=O)O]

The liquid compositions of the present invention utilize the (S)-(+)-enantiomer and the 2-cis-,4-trans-stereochemistry of the carbon chain rather than a racemic mixture of enantiomers and any of the other possible combinations of stereochemistry of the molecule. Unless expressly stated otherwise, in all instances when the Application refers to abscisic acid, S-ABA, or (S)-(+)-abscisic acid, it refers specifically to 2-cis-,4-trans-(S)-(+)-abscisic acid.

As used herein, all numerical values relating to amounts, weight percentages and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The phrase "effective amount" of a component means a sufficient amount of the component to provide the desired biological or chemical effect without at the same time causing additional negative effects. The amount of (S)-(+)-abscisic acid or of another formulation component that is "effective" will vary from composition to composition, depending on the particular agricultural use, the particular salt or salts, and the like. Thus, it is not always possible to specify an exact "effective amount." However, an appropriate "effective amount" in any individual case may be determined by one of ordinary skill in the art using routine experimentation.

Liquid compositions of the present invention can be prepared as either ready-to-use dilutions or dilutable concentrates. According to the present invention, a composition containing from 0.25% to as much as 45% by weight of (S)-(+)-abscisic acid can be obtained at a pH of about 6.0 to about 7.0. The dilutable concentrates can be diluted into water directly to a final application concentration or to any intermediate concentration, without risk of precipitation of the active ingredient as long as the buffering capacity of the composition is not exceeded. The liquid compositions of the present invention are safe to handle and use and the (S)-(+)-abscisic acid active ingredient is color stable and does not precipitate under various expected storage, shipping, and use conditions. Applicants' compositions are a significant improvement over formulations of the prior art for treating plants. A person having ordinary skill in the art would be able to determine how to prepare the final aqueous solution concentration for direct application to plants, or how to prepare any intermediate dilutions for use in chemigation equipment or injection diluters or similar equipment, without undue experimentation and without causing precipitation of the active ingredient or other formulation components. Similarly, a person having ordinary skill in the art would be able to determine an effective amount of ethephon to mix with the formulations of the present invention without undue experimentation should it be desired to apply a use solution containing both (S)-(+)-abscisic acid and ethephon.

The aqueous solution formulations of the present invention may also optionally include a substantial amount of an additional ingredient or several additional ingredients that enhance the biological activity of the (S)-(+)-abscisic acid. Such enhancing ingredients include, but are not limited to, urea, ammonium nitrate, ammonium acetate, calcium chloride, calcium nitrate and magnesium nitrate. The use of water as the solvent allows for a combined liquid formulation comprising any or several of these inorganic components or urea that may contain a level of the enhancing ingredient equal to the concentration of the (S)-(+)-abscisic acid salt or even up to 10 times the amount of (S)-(+)-abscisic acid by weight or more. This provides an advantage over the use of an organic solvent, in which these inorganic components or urea have little if any solubility.

The end user can apply compositions of the present invention to plants for various purposes, including but not limited to improving stress tolerance, improving water use efficiency, slowing the rate of water transpiration, temporarily reducing the growth rate, manipulating the flowering process, and improving the quality and color of fruits. The possible uses may also include, for example, distribution and sale of various concentrated solutions of (S)-(+)-abscisic acid. Utilizing such high concentrations for shipping and handling allows the use of smaller volumes of water, thus simplifying shipping and handling procedures and decreasing costs. The end user could then dilute the product to a 1% concentration (or other percentage depending on the end user's needs) and fill the supply reservoir of mixing equipment for spray or drench application to vegetable or ornamental plants for example. Alternatively, another end user could prepare a diluted solution for injection into a drip irrigation system for a vineyard at the appropriate time to enhance the color of a wine or table grape crop.

Applicants have found that the compositions containing (S)-(+)-abscisic acid as the potassium salt show significant improvement over formulations in the prior art for treating plants. Specifically, Applicants' have found that the compositions of this invention containing (S)-(+)-abscisic acid as the potassium salt can be used in a wide range of concentrations and on a wide range of crops. For example, the compositions of the present invention can be used to accelerate and enhance the development of red coloration in red grape berries, allowing harvesting to begin earlier than would otherwise be possible, and allowing for higher vineyard yields because fewer bunches remain unharvested due to poor coloration. The harvest quality parameters and the storage characteristics of the grapes treated before harvest with the compositions of the present invention alone or in combination with ethephon are superior to those of grapes treated with ethephon alone, which has been the accepted practice in the prior art. The compositions of the present invention can be applied to vegetable seedling transplants before and/or after transplanting to temporarily slow their growth, reduce transplant shock, enhance crop establishment after transplant, and increase the plant's resistance to stress events. Compositions of the present invention can be applied to leafy vegetables and herbs to slow their growth and manage the timing of harvest. Ornamental plants can be treated with the compositions of the present invention, significantly reducing transpiration and delaying wilting caused by environmental stress thereby resulting in more desirable plants compared to untreated plants.

An object of the present invention is to provide methods of treating plants comprising applying an effective amount of the compositions of the present invention to a plant or plant parts. In one embodiment, composition of the present invention can be applied to grapes or grape vines in one or more separate applications in order to enhance coloration of red grapes and/or modify the sensory characteristics of red or white grape berries. An effective amount of (S)-(+)-abscisic acid in an application solution for grapes and grapevines is from about 10 to about 10,000 ppm and the effective amount of (S)-(+)-abscisic acid applied per application is from about 25 to about 1000 g/Ha. More preferably, an effective amount of (S)-(+)-abscisic acid in an application solution for grapes and grapevines is about from about 100 to about 500 ppm and the effective amount of (S)-(+)-abscisic acid applied per application is from about 185 to about 370 g/Ha.

In another embodiment, compositions of the present invention can be mixed with an effective amount of ethephon. An effective amount of ethephon for application to grapes and grape vines is from about 140 to about 560 g/Ha. The embodiments of the present invention are suitable for tank mixing with an effective amount of other plant growth regulators besides ethephon without precipitation of the resulting mixture.

Compositions of the present invention may be used to treat vegetable crops in one or more applications to vegetable seedlings or older plants to reduce plant growth, reduce crop stress, and enhance post-harvest crop quality. Vegetable crops include, but are not limited to: fruiting vegetables such as tomato and pepper; cucurbits such as cucumbers and melons; brassica vegetables such as broccoli and cabbage; leafy vegetables and herbs such as celery, spinach, lettuce, beet greens, arugula and other leafy greens, fennel, basil and other herbs. An effective amount of (S)-(+)-abscisic acid in an application solution for vegetable seedlings or older plants is from about 25 to about 2,000 ppm and the effective amount of (S)-(+)-abscisic acid as the potassium salt applied per application is from about 0.047 to about 18.93 g per 100 sq. ft. for greenhouse applications and from about 11.7 to about 1871 g/Ha for field applications. More preferably, the effective amount of (S)-(+)-abscisic acid as the potassium salt in an application solution for vegetable seedlings or mature plants is from about 75 to about 1,000 ppm and the effective amount of (S)-(+)-abscisic acid as the potassium salt applied per application is from about 0.14 g to about 9.5 g per 100 sq ft. for greenhouse applications and from about 35.1 to about 935 g per Ha for field applications.

Compositions of the present invention may be used to treat ornamental crops such as potted flowers, bedding plants, perennial, nursery, and foliage plants in one or more applications by drench, sprench, spray, flood, or chemigation to reduce water use, conserve water, withstand environmental stress and control growth. An effective amount of (S)-(+)-abscisic acid as the potassium salt in an application solution for ornamental plants is from about 25 to about 2,000 ppm and the effective amount of (S)-(+)-abscisic acid as the potassium salt applied per application is from about 0.047 to about 5.678 g per 100 sq ft. More preferably, an effective amount of (S)-(+)-abscisic acid as the potassium salt in an application solution for ornamental plants is from about 125 to about 500 ppm and the effective amount of (S)-(+)-abscisic acid as the potassium salt applied per application is from about 0.237 to about 1.42 g per 100 sq ft.

Presently, the most preferred antimicrobial agent is potassium sorbate, however, suitable alternatives known by those skilled in the art may be used. When compositions of the present invention are intended for long term storage or for distribution and commercial sale to the user, it is advantageous to incorporate the antimicrobial agent at a concentration of from about 0.01% to about 1.0% by weight, more preferably from about 0.1 to about 0.75%, and most preferably at about 0.25%.

The concentration of the surfactant and precipitation inhibitor Altox™ 4913 in the compositions of the present invention can be from about 0.02% to about 40.0% by weight. The most preferred range of concentration for Atlox™ 4913 in the compositions of the present invention is from about 0.1 to about 1.0% by weight, with the most preferred amount at about 0.25%.

The concentration of the color stabilizers, sodium citrate and sodium acetate, in compositions of the present invention can be from about 0.1% to about 1.0%, and more preferably from about 0.25 to about 0.75%, with the most preferred amount being about 0.5% for each color stabilizer.

In one embodiment, the present invention relates to an aqueous composition for the treatment of plants comprising at least about 0.25% by weight of the composition of (S)-(+)-abscisic acid as the potassium salt, an effective amount of the surfactant Atlox™ 4913 as a precipitation inhibitor, and an effective amount of the color stabilizers sodium citrate and sodium acetate.

Another embodiment of the present invention is an aqueous composition that comprises from about 0.25 to about 45 weight % of (S)-(+)-abscisic acid as the potassium salt, from about 0.02 to about 40 weight % of the surfactant Atlox™ 4913 as a precipitation inhibitor, from about 0.01 to about 1.0 weight % of potassium sorbate, and from about 0.1 to about 1.0 weight % sodium citrate, from about 0.1 to about 1.0 weight % sodium acetate.

A further embodiment of the present invention is an aqueous composition that comprises from about 0.25 to about 45 weight % of (S)-(+)-abscisic acid as the potassium salt, from about 0.02 to about 40 weight % of the surfactant Atlox™ 4913 as precipitation inhibitor, from about 0.01 to about 1.0 weight % potassium sorbate, from about 0.1 to about 1.0 weight % sodium citrate, from about 0.1 to about 1.0 weight % sodium acetate, with from 5 to 50 weight % of a component or multiple components which enhance the biological activity of the (S)-(+)-abscisic acid, including but not limited to urea, ammonium nitrate, ammonium acetate, calcium chloride, or magnesium nitrate.

A more preferred embodiment of the present invention is an aqueous composition that comprises about 10.0 weight % of (S)-(+)-abscisic acid as the potassium salt, about 0.5 weight % of sodium citrate, about 0.5 weight % of sodium acetate, about 0.25 weight % of Atlox 4913™, about 0.25 weight % of potassium sorbate, and about 87.0 weight % of water.

In the preferred embodiments, the pH range of the concentrated compositions of the invention, and any aqueous solutions at final use dilution prepared from the concentrates, are from about 6.2 to about 6.6 and thereby slightly below neutral (pH 7).

The compositions of the present invention may also optionally include an effective amount of an additional ingredient or several additional ingredients in order to enhance the long-term chemical stability of the (S)-(+)-abscisic acid or the composition as a whole. The composition may optionally contain sodium sulfite, for example, from about 0.1 to about 0.5 weight %.

The ions in the formulation of the present invention are dissociated because it is a solution. As a result, once the solutions are prepared, it is no longer possible to analyze the compositions for the specific components, such as sodium acetate or potassium sorbate, that are combined to prepare them. However, the formulations and their use solutions can be characterized by ion concentrations. Thus a presently preferred embodiment of the present invention can comprise an aqueous composition with (S)-(+)-abscisic acid as a potassium salt at a concentration from about 0.25% to about 45.00% by weight, sorbate at a concentration from about 0.0007 M to about 0.0666 M, citrate at a concentration from about 0.0034 M to about 0.0340 M, acetate at a concentration from about 0.0122 M to about 0.1219 M, Atlox™ 4913 at a concentration from about 0.02% to about 10.00%, further comprising from about 0.0224 M to about 0.2239 M sodium, and from about 0.0101 M to about 1.7691 M potassium, and from about 35.34% to about 99.48% water, wherein the pH of the aqueous composition is from about 6.0 to about 7.0.

A more preferred embodiment of the present invention can comprise an aqueous composition with (S)-(+)-abscisic acid as a potassium salt at a concentration from about 5.0% to about 20.0% by weight, sorbate at a concentration from about 0.0067 M to about 0.0499M, citrate at a concentration from about 0.0085 M to about 0.0255 M, acetate at a concentration from about 0.0305 M to about 0.0914 M, Atlox™ 4913 at a concentration from about 0.10% to about 1.00%, further comprising from about 0.0560 M to about 0.1679 M sodium, and from about 0.1958 M to about 0.8066 M potassium, and from about 73.79% to about 93.56% water, wherein the pH of the aqueous composition is from about 6.0 to about 7.0.

The presently most preferred embodiment of the present invention comprises an aqueous composition wherein the (S)-(+)-abscisic acid as the potassium salt is at a concentration of about 10% by weight, sorbate is at a concentration of about 0.0166 M, citrate is at a concentration of about 0.0170 M, acetate is at a concentration of about 0.0610 M, Atlox™ 4913 is at a concentration of about 0.25% by weight, further comprising about 0.1120 M sodium ions, and about 0.3950 M potassium ions, and about 87.02% water by weight, wherein the pH of the aqueous composition is from about 6.1 to 6.6.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to make and use the invention. They are not intended to limit the invention or its protection in any way.

EXAMPLES

Example 1

Preparation of an Aqueous Formulation Composition of the Potassium salt of (S)-(+)-Abscisic Acid An aqueous formulation composition was prepared comprising (S)-(+)-abscisic acid (97.7%) at a concentration of about 10.2% (10%) by weight of the total volume. The solution also contained 0.25% by weight of potassium sorbate, 0.50% by weight of sodium citrate, 0.50% by weight of sodium acetate, 0.25% by weight of Atlox™ 4913, 4.50% by weight of potassium hydroxide, and 83.8% by weight of water. The solution had a final pH of about 6.0 to 6.6.

Example 2

Preparation of a Tank Mix of an Aqueous Formulation Composition of the Potassium Salt of (S)-(+)-Abscisic Acid with Ethephon A tank mix solution was produced by mixing 200 mL of standard water with about 10 grams of the Formulation of Example 1 to prepare a solution with an (S)-(+)-abscisic acid concentration of about 5000 ppm. Then about 9.22 grams of Ethrel® (21.7% ethephon), available from Bayer Crop Science, was added to the (S)-(+)-abscisic acid to give a tank mix solution with an ethephon concentration of about 10,000 ppm. The standard water used was World Health Organization ("WHO") standard water, prepared according to method WHO/M29.

The tank mix can be further diluted prior to application.

Example 3

Improved Solubility of (S)-(+)-Abscisic Acid-Ethephon Tank Mix Solution

The composition of the tank mix solution of Example 2 is resistant to precipitation compared to tank mix solutions of the prior art. Applicants found that when (S)-(+)-abscisic acid solutions of the prior art were mixed with ethephon prior to application to plants, (S)-(+)-abscisic acid would precipitate from the solution. As discussed above, precipitation is of major concern because the precipitated product may block the application system and render the solution unusable. Additionally, efficacy of the solution will be reduced due to lower concentrations of the (S)-(+)-abscisic acid and ethephon active ingredients. Applicants prepared the Formulation of Example 1 without surfactant and then diluted the formulation to form a 5000 ppm (S)-(+)-abscisic acid solution. Three samples of this solution were mixed with three different surfactants. Then ethephon was added to each solution to give a 10,000 ppm concentration of ethephon. Applicants surprisingly discovered that the surfactant Atlox™ 4913 prevented precipitation from occurring in the tank mix solution, as seen below in Table I. Other surfactants were ineffective in preventing precipitation. In fact, greater amounts of precipitate formed in tank mixes of ethephon with the Formulation of Example 1 (without surfactant) plus the surfactants Tween® 20 or Brij® 98 compared to a tank mix prepared of Formulation of Example 1 (without surfactant) plus ethephon. Precipitation occurred within as little as 4 hours. Precipitation occurred more quickly at 5° C. vs. 25° C.

TABLE I

Amount of (S)-(+)-Abscisic Acid Precipitation in (S)-(+)-Abscisic Acid - Ethephon Tank Mixtures (200 ml samples)

| (S)-(+)-Abscisic Acid - Ethephon Tank Mixture | (S)-(+)-Abscisic Acid Precipitation at 5° C. | (S)-(+)-Abscisic Acid Precipitation at 25° C. |
|---|---|---|
| with Atlox ™ 4913 (0.25%) | No precipitation | No precipitation |
| with Tween ® 20 (0.10%) | 0.324 g. (3.24% of original S-ABA) | 0.279 g. (2.79% of original S-ABA) |
| with Brij ® 98 (0.25%) | 0.380 g. (3.80% of original of S-ABA) | 0.343 g. (3.43% of original S-ABA) |
| No surfactant added | 0.298 g (2.98% of original S-ABA) | Trace of precipitation |

Thus, it has been demonstrated that the addition of Atlox™ 4913 eliminated precipitation when (S)-(+)-abscisic acid is tank mixed with ethephon.

Example 4

Increased Control of Microbial Growth

The aqueous Formulation of Example 1 was subjected to microbial testing to determine its susceptibility to microbial growth compared to other compositions utilizing either no surfactant or different surfactants. (S)-(+)-abscisic acid requires a pH above about 6.0 to be efficiently solubilized. At these pHs, most preservatives are ineffective for controlling microbial growth, particularly growth of yeasts and molds. Inclusion of Atlox™ 4913 in the aqueous Formulation of Example 1 allows the pH of the formulation to be adjusted lowered to pH levels where preservatives are more effective at controlling microbial growth while avoiding precipitation of (S)-(+)-abscisic acid from the solution.

TABLE II

Bio-Load of (S)-(+)-abscisic acid aqueous formulations at different pH levels with and without Atlox ™ 4913

| | pH of solution | Yeast/Mold Bio-Load |
|---|---|---|
| Formulation of Example 1 | 6.2 | No growth on Potato Dextrose Agar |
| Formulation of Example 1 with Tween ® 20 instead of Atlox ™ 4913 | 6.6 | 100+ spores/ml on Potato Dextrose Agar |
| Formulation of Example 1 without a surfactant | 6.6 | 100+ spores/ml on Potato Dextrose Agar |

These data demonstrate that the Formulation of Example 1 has superior microbial growth control compared to prior art formulations.

Example 5

Increased Solubility of (S)-(+)-Abscisic Acid at a Lower pH

It is known in the art that (S)-(+)-abscisic acid is less soluble as the pH approaches its pKa. The pKa of (S)-(+)-abscisic acid is about 4.7 and the solubility in water at a pH at or below the pKa is about 3000 ppm. Applicants determined the solubility of (S)-(+)-abscisic acid in dilutions of the aqueous Formulation of Example 1 at various pH values and compared this with the solubility of (S)-(+)-abscisic acid of dilutions of aqueous formulation compositions utilizing different surfactants. Applicants surprisingly discovered that high concentrations of (S)-(+)-abscisic acid can be maintained at a lower pH with Atlox™ 4913 as a dispersant and surfactant. The solubility of (S)-(+)-abscisic acid in dilutions of various formulations with and without Atlox™ 4913 is shown in Table III.

TABLE III

| | Concentration of (S)-(+) abscisic acid in solution, pH 2.35 |
|---|---|
| Formulation of Example 1 | 5000 ppm (S)-(+)-abscisic acid with no precipitation |
| Formulation of Example 1 with Tween ® 20 instead of Atlox ™ 4913 | precipitation occurs at 3600 ppm (S)-(+)-abscisic acid |
| Formulation of Example 1 prepared without a surfactant | precipitation occurs at 2800 ppm (S)-(+)-abscisic acid |

These data demonstrate that the inclusion of Atlox™ 4913 in the Formulation of Example 1 increases the solubility of (S)-(+) abscisic acid at a lower pH value.

Example 6

Increased Color Stability

Applicants found that solutions of the prior art lacked color stability. Applicants also found that additives such as sulfites gave excellent color stability, but sulfites are unacceptable for inclusion in products used on food crops. Therefore, there is a need for effective, safe and color stabilized (S)-(+)-abscisic acid formulations. Three different formulation compositions were tested to determine the effect of the color stabilizing additives in each composition. The Formulation of Example 1 contained the color stabilizers sodium citrate and sodium acetate. The formulation composition VBC-30101 contained (S)-(+)-abscisic acid as the ammonium salt, potassium sorbate, Tween® 20, and the color stabilizers sodium sulfite and sodium citrate. The formulation composition VBC-30074 contained (S)-(+)-abscisic acid as the ammonium salt, potassium sorbate, and no color stabilizers. The formulation compositions were subjected to high temperature conditions (54° C.) to accelerate the development of discoloration. The color of the formulations were then visually rated using the Gardner color scale, in which the numeric values range from 1 (near colorless) to 18 (deeply colored). As can be seen below in Table IV, the Formulation of Example 1 provides superior color stability under extreme conditions and is highly resistant to discoloration.

TABLE IV

Color stability testing

Gardner chart color rating of sample after incubation at 54° C. for various storage times: (Higher numbers reflect a darker color) (A reading of 1 or below is essentially colorless when graded using Gardner Scale cuvets)

|  | Two weeks | Three weeks | Four weeks |
| --- | --- | --- | --- |
| Formulation of Example 1 | <1 | 1 | 1 |
| VBC-30101 | 1 | 1 to 3 | 4 to 8 |
| VBC-30074 | 8 to 11 | 9 to 13 | 12 to 14 |

The invention claimed is:

1. A method of treating a plant comprising applying to the plant an effective amount of an aqueous composition comprising at least about 0.25 weight % of the composition of (S)-(+)-abscisic acid as a potassium salt, an effective amount of sodium citrate, an effective amount of sodium acetate, an effective amount of an acrylic copolymer solution, an effective amount of potassium sorbate, and optionally one or more performance enhancing additives.

2. The method of claim 1 wherein the plant is selected from the group consisting of grapes, vegetables and ornamental plants.

3. The method of claim 2 wherein the plant is grapes.

4. The method of claim 3 wherein the (S)-(+)-abscisic acid as the potassium salt is applied at a rate of from about 25 to about 1,000 grams per hectare (g/Ha).

5. The method of claim 3 wherein the (S)-(+)-abscisic acid as the potassium salt is applied at a rate of from about 183 to about 370 g/Ha.

6. The method of claim 3 wherein the (S)-(+)-abscisic acid as the potassium salt is applied at a concentration of from about 10 to about 10,000 parts per million (ppm).

7. The method of claim 3 wherein the (S)-(+)-abscisic acid as the potassium salt is applied at a concentration of from about 100 to about 500 ppm.

8. The method of claim 2 wherein the plant is a vegetable.

9. The method of claim 8 wherein the vegetable is selected from the group consisting of fruiting vegetables, cucurbits, brassica vegetables, leafy vegetables and herbs.

10. The method of claim 8 wherein the (S)-(+)-abscisic acid as the potassium salt is applied to the vegetables in a greenhouse at rate of from about 0.047 to about 18.93 grams per 100 square feet (g/100ft$^2$).

11. The method of claim 8 wherein the (S)-(+)-abscisic acid as the potassium salt is applied to the vegetables in a field at a rate of from about 11.7 to about 1,871 grams per hectare (g/Ha).

12. The method of claim 2 wherein the plant is an ornamental plant.

13. The method of claim 12 wherein the ornamental plant is selected from the group consisting of potted flowers, bedding plants, perennials, nursery plants and foliage plants.

14. The method of claim 12 wherein the (S)-(+)-abscisic acid as the potassium salt is applied at a rate of from about 0.047 to about 5.678 grams per 100 square feet (g/100ft$^2$).

15. A method of treating a plant comprising applying to the plant an effective amount of an aqueous composition comprising from about 0.25 to about 45.0 weight % of (S)-(+)-abscisic acid as a potassium salt, from about 0.1 to about 1.0 weight % of sodium citrate, from about 0.1 to about 1.0 weight % of sodium acetate, from about 0.02 to about 40.0 weight % of an acrylic copolymer solution, and from about 0.01 to about 1.0 weight % of potassium sorbate.

16. The method of claim 15 wherein the composition comprises from about 5 to about 20 weight % of (S)-(+)-abscisic acid as the potassium salt, from about 0.25 to about 0.75 weight % of sodium citrate, from about 0.25 to about 0.75 weight % of sodium acetate, from about 0.10 to about 1.0 weight % of an acrylic copolymer solution, and from about 0.1 to about 0.75 weight % of potassium sorbate.

17. The method of claim 16 wherein the composition comprises about 10.0 weight % of (S)-(+)-abscisic acid as the potassium salt, about 0.5 weight % of sodium citrate, about 0.5 weight % of sodium acetate, about 0.25 weight % of an acrylic copolymer solution, about 0.25 weight % of potassium sorbate and about 87.0 weight % of water.

18. A method of treating a plant comprising applying to the plant an effective amount of an aqueous composition comprising from about 0.25 to about 45.00 weight % of (S)-(+)-abscisic acid as a potassium salt, from about 0.0007 to about 0.0666 M sorbate, from about 0.0034 to about 0.0340 M citrate, from about 0.0122 to about 0.1219 M acetate, from about 0.02 to about 10.00 weight % of an acrylic copolymer solution, from about 0.0224 to about 0.2239 M sodium, from about 0.0101 to about 1.7691 M potassium, and from about 35.34 to about 99.48 weight % of water, wherein the pH of the aqueous composition is from about 6.0 to about 7.0.

19. The method of claim 18 wherein the composition comprises from about 5.0 to about 20.0 weight % of (S)-(+)-abscisic acid as the potassium salt, from about 0.0067 to about 0.0499 M sorbate, from about 0.0085 to about 0.0255 M citrate, from about 0.0305 to about 0.0914 M acetate, from about 0.1 to about 1.00 weight % of an acrylic copolymer solution, from about 0.0560 to about 0.1679 M sodium, from about 0.1958 to about 0.8066 M potassium, and from about 73.79 to about 93.56 weight % of water.

20. The method of claim 19 wherein the composition comprises about 10 weight % of (S)-(+)-abscisic acid as the potassium salt, about 0.0166 M sorbate, about 0.0170 M citrate, about 0.0610 M acetate, about 0.25 weight % of an acrylic copolymer solution, about 0.1120 M sodium, about 0.3950 M potassium, and about 87.02 weight % of water, wherein the pH of the aqueous composition is from about 6.1 to about 6.6.

* * * * *